US011020072B2

(12) United States Patent
Narayanaswamy et al.

(10) Patent No.: US 11,020,072 B2
(45) Date of Patent: Jun. 1, 2021

(54) SYSTEM AND METHOD FOR REGULATING TEMPERATURE OF IMAGING DETECTOR SENSORS

(71) Applicant: GE PRECISION HEALTHCARE LLC, Wauwatosa, WI (US)

(72) Inventors: Mahesh Raman Narayanaswamy, Milwaukee, WI (US); Habib Vafi, Brookfield, WI (US); Nicholas Ryan Konkle, Sussex, WI (US); Brian Joseph Graves, Waukesha, WI (US)

(73) Assignee: GE PRECISION HEALTHCARE LLC, Wauwatosa, WI (US)

( * ) Notice: Subject to any disclaimer, the term of this patent is extended or adjusted under 35 U.S.C. 154(b) by 44 days.

(21) Appl. No.: 16/437,244

(22) Filed: Jun. 11, 2019

(65) Prior Publication Data

US 2020/0390410 A1    Dec. 17, 2020

(51) Int. Cl.
*A61B 6/00*    (2006.01)
*A61B 6/03*    (2006.01)
*G01T 1/20*    (2006.01)
*G01T 7/00*    (2006.01)
*G01T 1/161*   (2006.01)

(52) U.S. Cl.
CPC ............ *A61B 6/4488* (2013.01); *A61B 6/032* (2013.01); *A61B 6/4233* (2013.01); *G01T 1/161* (2013.01); *G01T 1/2018* (2013.01); *G01T 7/00* (2013.01)

(58) Field of Classification Search
None
See application file for complete search history.

(56) References Cited

U.S. PATENT DOCUMENTS

| 7,161,157 | B2 | 1/2007 | Lacey | |
|---|---|---|---|---|
| 9,086,360 | B2 | 7/2015 | Joshi | |
| 2003/0016779 | A1* | 1/2003 | Pohan | A61B 6/035 378/19 |
| 2017/0059720 | A1* | 3/2017 | McBroom | G01T 1/2985 |
| 2019/0350545 | A1* | 11/2019 | Ikhlef | G01T 1/2018 |
| 2019/0383954 | A1* | 12/2019 | Onouchi | A61B 6/032 |

\* cited by examiner

*Primary Examiner* — Hoon K Song
(74) *Attorney, Agent, or Firm* — Fletcher Yoder, P.C.

(57) ABSTRACT

A detector assembly positionable to receive X-rays from an X-ray source within an imaging system is provided. The detector assembly includes multiple detector elements. The detector assembly also includes a temperature regulation system including multiple temperature regulation devices, wherein each temperature regulation device of the multiple temperature regulation devices is associated with a respective detector element of the multiple detector elements, and each temperature regulation device is configured to independently maintain a consistent temperature across a portion of a respective detector element.

18 Claims, 6 Drawing Sheets

SYSTEM AND METHOD FOR REGULATING TEMPERATURE OF IMAGING DETECTOR SENSORS

BACKGROUND

The subject matter disclosed herein relates to imaging systems, and more particularly, to regulating a temperature of detector sensors.

In computed tomography (CT), X-ray radiation spans a subject of interest, such as a human patient, and a portion of the radiation impacts a detector where the image data is collected. In digital X-ray systems a photodetector produces signals representative of the amount or intensity of radiation impacting discrete pixel regions of a detector surface. The signals may then be processed to generate an image that may be displayed for review. In the images produced by such systems, it may be possible to identify and examine the internal structures and organs within a patient's body. In CT systems a detector array, including a series of detector elements or sensors, produces similar signals through various positions as a gantry is displaced around a patient, allowing volumetric reconstructions to be obtained.

CT imaging system may include a solid-state detector that includes an array of photodiodes that detect light impulses from an array of scintillation crystals. The photodiodes are typically mounted in close proximity to readout electronics to preserve the signal integrity of the photodiodes. In operation, the readout electronics generate heat that may affect the operation of the photodiodes. Accordingly, it is desirable to provide cooling for the CT detector. However, conventional cooling systems are more costly and complex and provide cooling for the detector array overall, as opposed to individual detector elements, which results in a slower thermal response.

BRIEF DESCRIPTION

Certain embodiments commensurate in scope with the originally claimed subject matter are summarized below. These embodiments are not intended to limit the scope of the claimed subject matter, but rather these embodiments are intended only to provide a brief summary of possible forms of the subject matter. Indeed, the subject matter may encompass a variety of forms that may be similar to or different from the embodiments set forth below.

In accordance with one embodiment, a detector assembly positionable to receive X-rays from an X-ray source within an imaging system is provided. The detector assembly includes multiple detector elements. The detector assembly also includes a temperature regulation system including multiple temperature regulation devices, wherein each temperature regulation device of the multiple temperature regulation devices is associated with a respective detector element of the multiple detector elements, and each temperature regulation device is configured to independently maintain a consistent temperature across a portion of a respective detector element.

In accordance with another embodiment, a computed tomography (CT) detector assembly is provided. The CT detector assembly includes a detector element. The detector element includes a scintillator array configured to convert X-rays into lower energy light photons, a photodiode array configured to convert the light photons into analog electrical signals, electronics configured to receive the analog electrical signals and to convert the analog electrical signals to digital signals, and a flex circuit coupled to both the photodiode array and the electronics and configured to provide the analog electrical signals to the electronics. The detector element also includes a thermal shunt coupled to the electronics and configured to receive heat generated by the electronics, a thermal isolation layer disposed between the photodiode array and the thermal shunt and configured to thermally isolate the electronics and the thermal shunt from the photodiode array, and a portion of the flex circuit is disposed between photodiode array and the thermal isolation layer. The CT detector assembly also includes a temperature regulation device coupled to the detector element and configured to maintain a consistent temperature across the photodiode array.

In accordance with a further embodiment, a computed tomography (CT) imaging system is provided. The CT imaging system includes a gantry having an opening for receiving an object to be scanned, an X-ray source attached to the gantry and configured to emit X-rays through the opening, and a detector assembly attached to the gantry and configured to receive the X-rays. The detector assembly includes a detector element that includes a scintillator array configured to convert X-rays into lower energy light photons, a photodiode array configured to convert the light photons into analog electrical signals, electronics configured to receive the analog electrical signals and to convert the analog electrical signals to digital signals, and a flex circuit coupled to both the photodiode array and the electronics and configured to provide the analog electrical signals to the electronics. The detector element also includes a thermal shunt coupled to the electronics and configured to receive heat generated by the electronics, a thermal isolation layer disposed between the photodiode array and the thermal shunt and configured to thermally isolate the electronics and the thermal shunt from the photodiode array, and a portion of the flex circuit is disposed between the photodiode array and the thermal isolation layer. The detector assembly also includes a temperature regulation device coupled to the detector element and configured to maintain a consistent temperature across the photodiode array.

BRIEF DESCRIPTION OF THE DRAWINGS

These and other features, aspects, and advantages of the disclosed subject matter will become better understood when the following detailed description is read with reference to the accompanying drawings in which like characters represent like parts throughout the drawings, wherein.

DETAILED DESCRIPTION

One or more specific embodiments will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present subject matter, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

Various embodiments provide an imaging system (e.g., computed tomography (CT) imaging system) that includes a temperature regulation system that provides temperature regulation for individual detector elements or sensors (e.g., via localized control and feedback). In certain embodiments, the temperature regulation system includes individual temperature regulation devices associated with each individual detector element that independently maintain a consistent temperature across a photodiode array of the detector element. Each detector element may include a thermal isolation layer and a thermal shunt (e.g., heat sink) that keeps heat generated by electronics away from the photodiode array of the detector element. The temperature regulation device may include a plurality of heating elements (e.g., resistor arrays) and associated thermistors integrated within a flex circuit, where the heating elements heat the photodiode array to a specified temperature and the thermistors provide temperature feedback. In certain embodiments, the temperature regulation device includes a semiconductor positive temperature coefficient (PTC) heater that self-regulates the PTC heater temperature to keep the photodiode array at a specified temperature. The temperature regulation system may enable a faster thermal response for the entire detector, which corresponds to a faster time for the overall CT system to be ready for acquisition. In addition, the temperature regulation system provides a lower cost thermal solution than typical cooling systems. Although the following techniques are described within the context of a CT imaging system, the temperature regulation system may be utilized with other imaging systems, such as a positron emission tomography imaging system or ultrasound imaging system.

Figure 1:
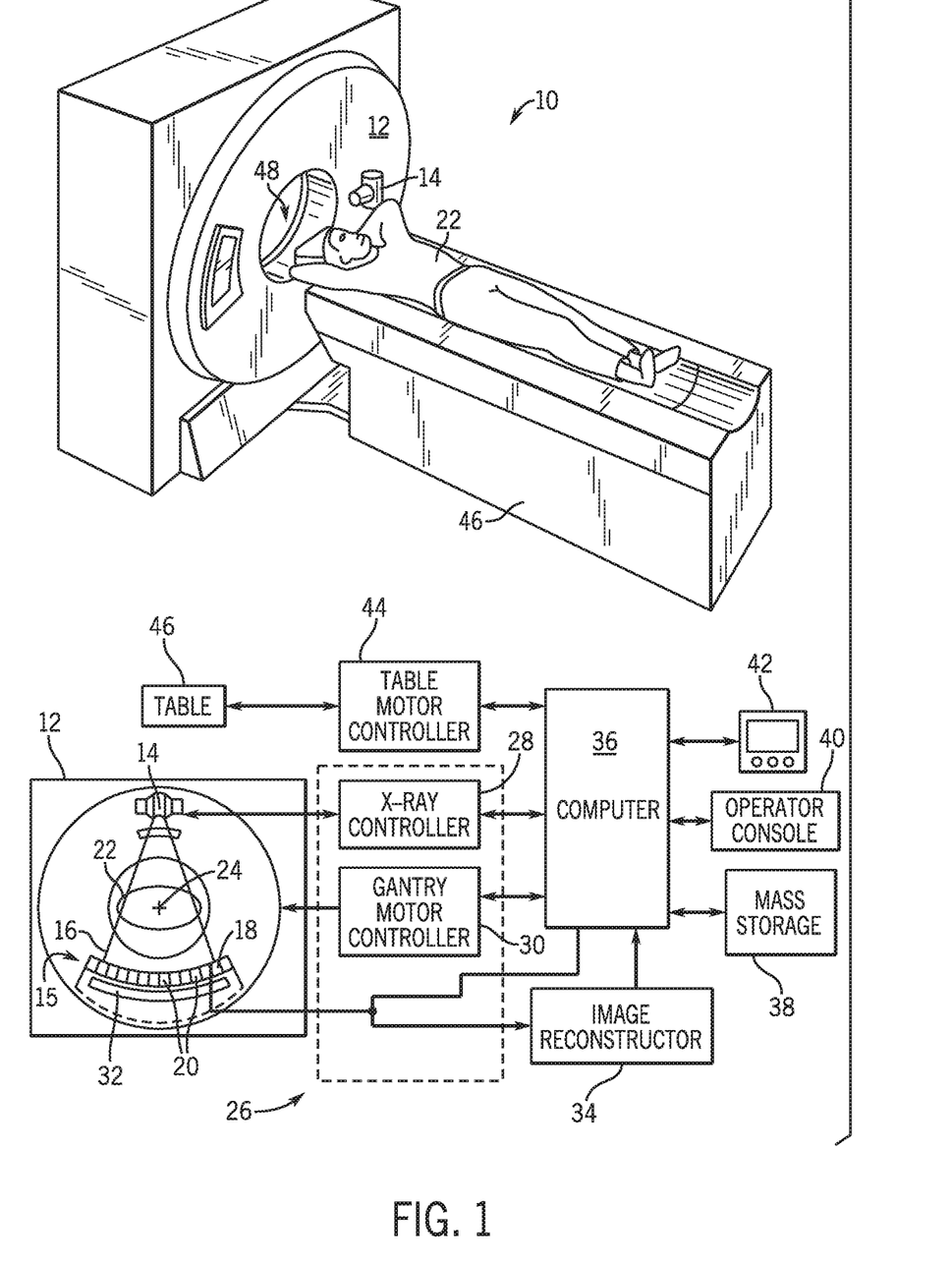
FIG. 1 is a combined pictorial view and block diagram of a computed tomography (CT) imaging system as discussed herein.

With the preceding in mind and referring to FIG. 1, a CT imaging system 10 is shown, by way of example. The CT imaging system includes a gantry 12. The gantry 12 has an X-ray source 14 that projects a beam of X-rays 16 toward a detector assembly 15 on the opposite side of the gantry 12. The detector assembly 15 includes a collimator assembly 18, a plurality of detector modules 20 (e.g., detector elements or sensors), and data acquisition systems (DAS) 32. The plurality of detector modules 20 detect the projected X-rays that pass through a patient 22, and DAS 32 converts the data to digital signals for subsequent processing. Each detector module 20 in a conventional system produces an analog electrical signal that represents the intensity of an incident X-ray beam and hence the attenuated beam as it passes through the patient 22. During a scan to acquire X-ray projection data, gantry 12 and the components mounted thereon rotate about a center of rotation 24 so as to collect attenuation data from a multitude of view angles relative to the imaged volume.

Rotation of gantry 12 and the operation of X-ray source 14 are governed by a control mechanism 26 of CT system 10. Control mechanism 26 includes an X-ray controller 28 that provides power and timing signals to an X-ray source 14 and a gantry motor controller 30 that controls the rotational speed and position of gantry 12. An image reconstructor 34 receives sampled and digitized X-ray data from DAS 32 and performs high-speed reconstruction. The reconstructed image is applied as an input to a computer 36, which stores the image in a mass storage device 38. Computer 36 also receives commands and scanning parameters from an operator via console 40. An associated display 42 allows the operator to observe the reconstructed image and other data from computer 36. The operator supplied commands and parameters are used by computer 36 to provide control signals and information to DAS 32, X-ray controller 28, and gantry motor controller 30. In addition, computer 36 operates a table motor controller 44, which controls a motorized table 46 to position patient 22 and gantry 12. Particularly, table 46 moves portions of patient 22 through a gantry opening or bore 48.

Figure 2:
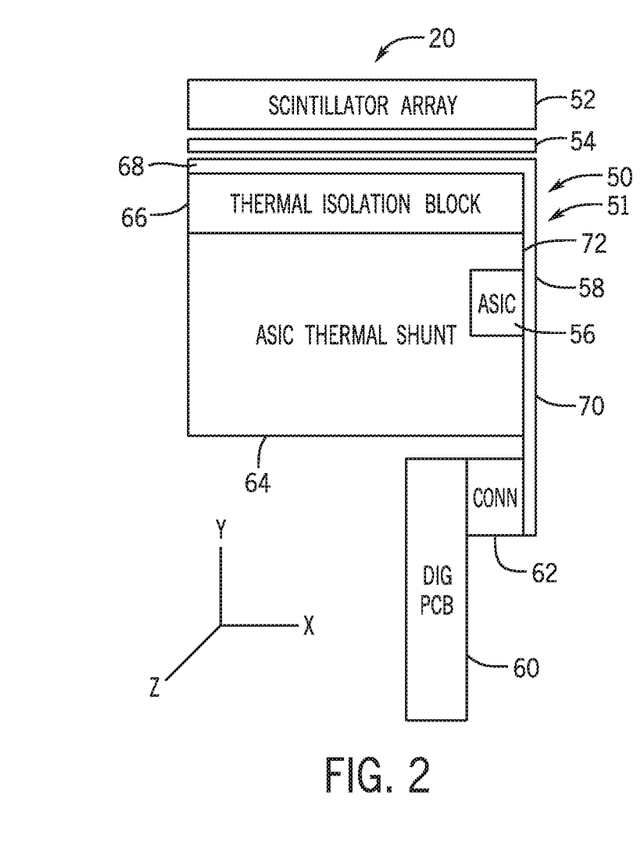
FIG. 2 is a schematic diagram of a side of a detector sensor assembly having a temperature regulation system, in accordance with an embodiment.

FIG. 2 is a schematic diagram of a side of the detector sensor assembly 20 (e.g., detector module or detector element) having a temperature regulation system 50. The temperature regulation system 50 may include a plurality of temperature regulation device 51 with each temperature regulation device associated with a respective detector sensor assembly 20. Each temperature regulation device 51 may independently regulate or maintain a temperature across a portion (e.g., photodiode array) of a respective detector sensor assembly 20. In certain embodiments, the temperature regulation device 51 is configured to receive feedback related to a respective temperature of a respective detector sensor assembly 20 and to control or regulate the temperature of the respective detector sensor assembly 20 based on the feedback. In certain embodiments, the temperature regulation device 51 may include heating elements (e.g. resistor arrays) disposed within a flex circuit adjacent a photodiode array. In certain embodiments, the temperature regulation device may include a positive temperature coefficient (PTC) heater disposed within or adjacent the flex circuit near the photodiode array.

The detector sensor assembly 20 includes a scintillator array 52, a photodiode array 54, and electronics 56 (e.g., one or more application specific integrated circuitry (ASIC) packages). As depicted, the photodiode array 54 is disposed beneath the scintillator array 52. The scintillator array 52 may formed of one or more scintillator crystals that are configured to convert X-rays into lower energy light photons (i.e., absorb the X-rays and emit absorbed in the form of light). The photodiode array 54 includes one or more photodiodes that receive and convert the light photons into corresponding electrical signals (e.g., analog electrical signals) that are used to reconstruct an image of an object being scanned. The electronics 56 are configured to receive the analog electrical signals and convert them to digital signals. The electronics 56 may include circuitry for readout, amplification, and analog-to-digital (A/D) conversion (e.g., linear A/D conversion).

The detector sensor assembly 20 includes a flex circuit 58 (e.g., single flex circuit) coupled mechanically and electrically to both the photodiode array 54 and the electronics 56. The flex circuit 58 provides the analog electrical signals to the electronics 56. The flex circuit 58 is coupled to a digital printed circuit board (PCB) 60 via a digital connector 62. The digital PCB 60 may include control circuitry that is utilized in the acquisition of the image data from the detector sensor assembly 20, receiving feedback from the temperature regulation device 51, and controlling or regulating the temperature regulation device 51. The flex circuit 58 provides the digital signals from the electronics 56 to the digital PCB 60. In addition, the flex circuit 58 provides signals to and from the temperature regulation device 51 to the digital PCB 60.

Figure 3:
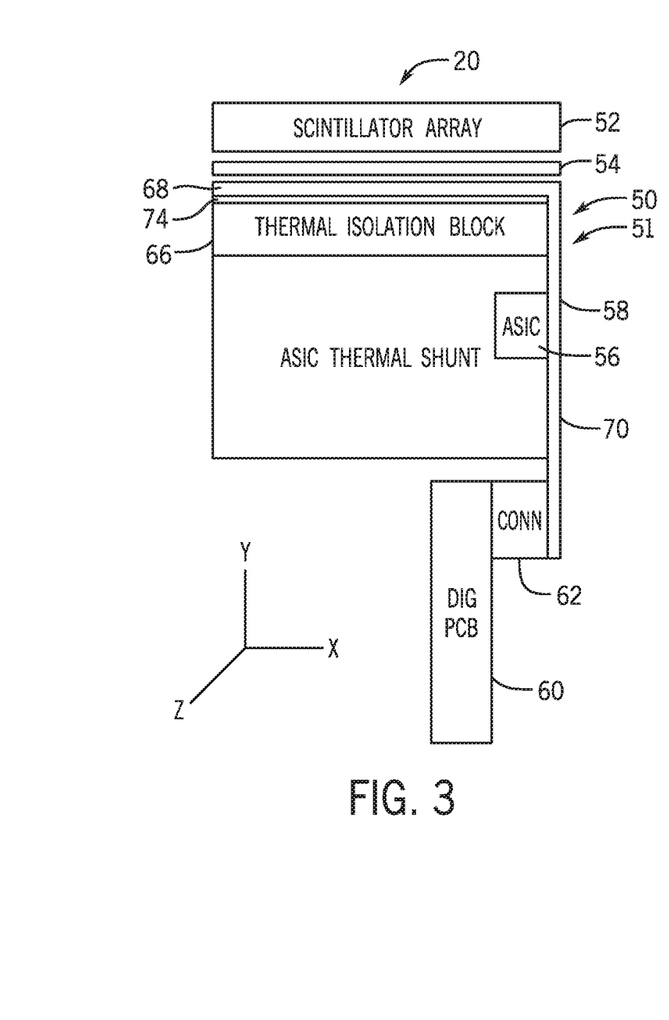
FIG. 3 is a schematic diagram of a side of a detector sensor assembly having a temperature regulation system (e.g., having a heat spreading layer), in accordance with an embodiment.

The detector sensor assembly 20 also includes a thermal shunt (e.g., ASIC thermal shunt) or heat sink 64. The thermal shunt 64 is coupled to the electronics 56. The thermal shunt 64 receives or absorbs heat generated by the electronics 56. The thermal shunt 64 may be thermally coupled to components of the detector assembly 15 (e.g., rails, frame, etc.) to transfer heat from the electronics 56 to these components. The thermal shunt 64 may be made of aluminum, copper, aluminum nitride, or any other thermally conductive metal. The detector sensor assembly 20 further includes a thermal isolation layer or block 66 to thermally isolate the electronics 56 and the thermal shunt 64 from the photodiode array 54. The thermal isolation layer 66 may be made of a glass reinforced epoxy laminate material (e.g., FR-4), thermoplastics (e.g., polyoxymethylene) or any other electrically insulating material. The thermal isolation layer 66 is disposed between the thermal shunt 64 and the flex circuit 58. In particular, a first portion 68 of the flex circuit 58 extends over the thermal isolation layer 66 between the thermal shunt 64 and the photodiode array 54, while a second portion 70 of the flex circuit 58 extends along a side 72 of the thermal isolation layer 66 and the thermal shunt 64 to the digital connector 62. In certain embodiments (see FIG. 3), a heat spreading layer 74 may be disposed between the portion 68 of the flex circuit 58 and the thermal isolation layer 66. The heat spreading layer 74 may be made of graphite or graphene.

Figure 4:
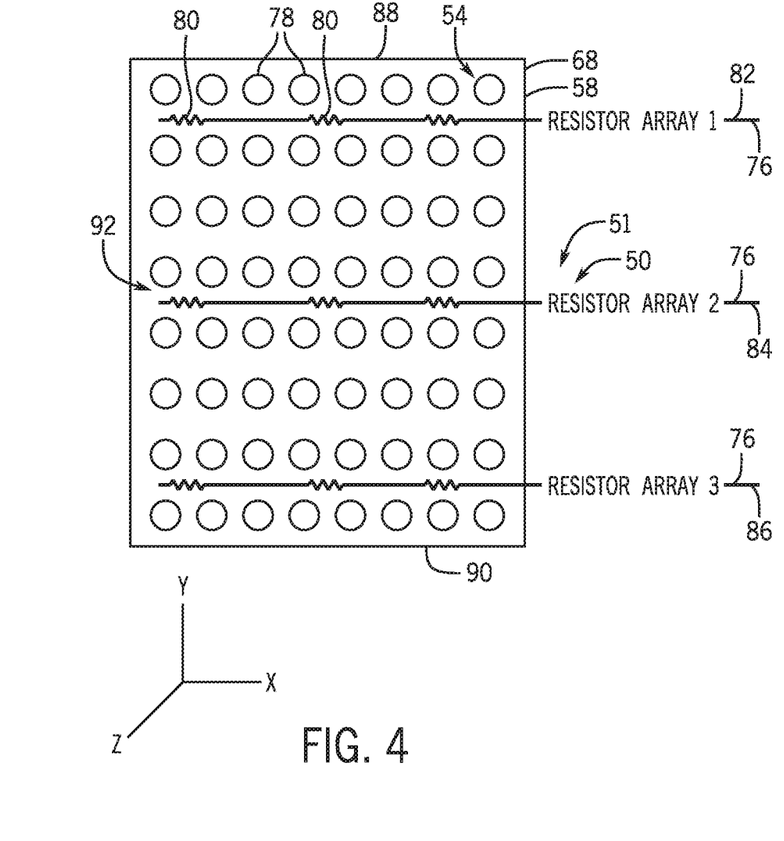
FIG. 4 is a schematic diagram illustrating a photodiode array of the detector sensor assembly of FIG. 2 in relation to a portion of the flex circuit having a temperature regulation device (e.g., heating elements), in accordance with an embodiment.

FIG. 4 is a schematic diagram (e.g., top view) illustrating the photodiode array 54 of the detector sensor assembly 20 of FIG. 2 in relation to the portion 68 of the flex circuit 58 having the temperature regulation device 51 (e.g., heating elements 76). As depicted, the photodiode array 54 includes a plurality of photodiodes 78 spaced apart from each other. The temperature regulation device 51 includes a plurality of heating elements 76 integrated within and extending across the portion 68 of the flex circuit 58 between the photodiodes 78 of the photodiode array 54. In response to signals from the control circuitry (e.g. on the digital PCB 60), the heating elements 76 may be heated to maintain a consistent temperature (or temperature range) across the photodiode array 54. As depicted, the heating elements 76 extend in an x-direction (e.g., relative to a plane parallel to the portion 68 of the flex circuit 58). In certain embodiments, the heating elements 76 may extend in a y-direction (e.g., orthogonal to the x-direction (within the plane parallel to the portion 68 of the flex circuit 58) or both in the x- and y-directions. Each heating element 76 includes a plurality of resistors 80 (e.g., array of resistors). As depicted, three heating elements 76 (heating elements 82, 84, 86) are depicted within the portion 68 of the flex circuit 58. The number of heating elements 76 may vary (e.g., 2, 3, 4, 5 or more heating elements 76). As depicted, the heating elements 82, 84 are respectively disposed adjacent edges 88, 90 of the portion 68 of the flex circuit 58, while the heating element 86 is centrally located as indicated by arrow 92. In certain embodiments, each heating element 76 may be utilized to keep the temperature at the same temperature set point or range. In other embodiments, different heating elements 76 may be utilized to keep the temperature at different set points or ranges depending on the location of the heating elements 76. For example, heating elements 82, 86 near the edges 88, 90 may be part of control loops that keep the temperature at a first temperature set point or range, while the heating element 84 may be part of a control loop that keeps the temperature at a second temperature set point or range that is different from the first temperature set point or range.

The time for a detector to reach thermal stability either from a cold start or a system reboot is significant and may cause delays in patient scanning. However, since the heating elements 76 are disposed adjacent the photodiode array 54, the temperature regulation device 51 provides significantly faster temperature control comparted to typical cooling techniques. In addition, the need for external heating and heating elements is eliminated for the detector sensor due to the temperature regulation device 51. The self-heating of the detector sensor (via the temperature regulation device 51) may be sufficient for precise temperature regulation.

Figure 5:
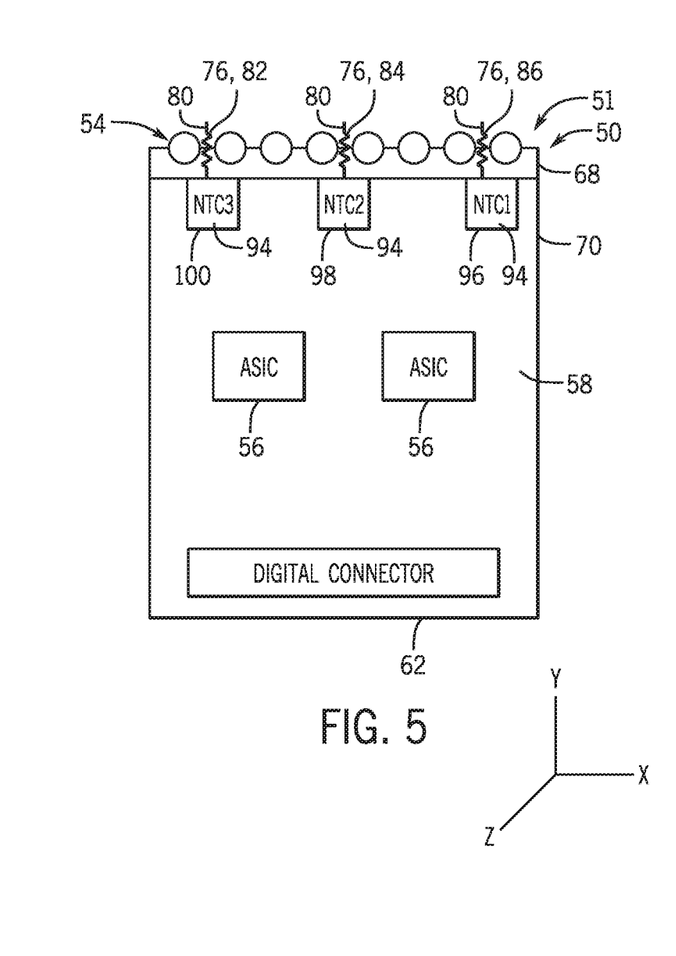
FIG. 5 is a schematic diagram illustrating a remaining portion of the flex circuit in FIG. 4 having the temperature regulation device, in accordance with an embodiment.

FIG. 5 is a schematic diagram illustrating the remaining portion 70 of the flex circuit 58 in FIG. 4 having the temperature regulation device 51. The portion 68 of the flex circuit 58 has the heating elements 76 of the temperature regulation device 51 as described in FIG. 4. As depicted in FIG. 5, the portion 70 of the flex circuit 58 is coupled to the electronics 56 (e.g., multiple ASIC packages) and the digital connector 62 as described above. In addition, a plurality of temperature sensors or thermistors 94 are embedded within the portion 70 of the flex circuit 58. In certain embodiments, the thermistors 94 may be negative temperature coefficient thermistors. As depicted, three thermistors 94 (thermistors 96 (NTC1), 98 (NTC2), 100 (NTC3)) are depicted within the portion 70 of the flex circuit 58. The number of thermistors 94 may vary (e.g., 2, 3, 4, 5 or more thermistors) based on the number of heating elements 76. The thermistors 96, 98, 100 are respectively coupled to the heating elements 82, 84, 86. The thermistors 94 provide temperature feedback (via changes in resistance) from the areas where they are located. Based on the temperature feedback from the thermistors 94, the control circuitry associated with the digital PCB 60 may adjust the heating of the heating elements 76. For example, the control circuitry may adjust the respective heating of each heating element 76 based on the respective feedback of the respective thermistor 94 associated within the heating element 76. The architecture of the thermal regulation device 51 reduces temperature gradients across the detector sensor.

Figure 6:
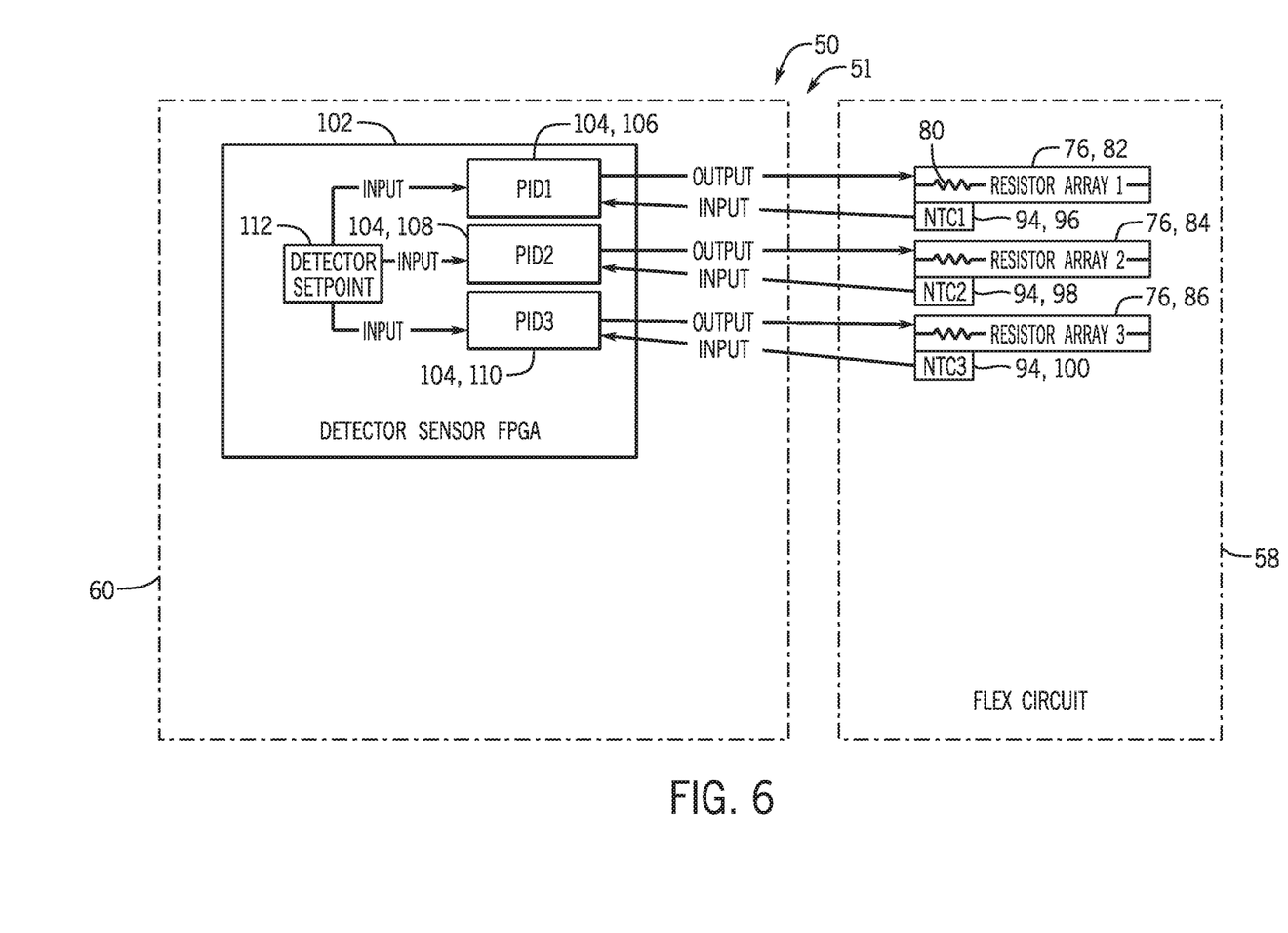
FIG. 6 is a schematic diagram of a control structure for a temperature regulation device in FIGS. 4 and 5, in accordance with an embodiment.

FIG. 6 is a schematic diagram of a control structure for the temperature regulation device 51 in FIGS. 4 and 5. The flex circuit 58 includes the heating elements 76 and the thermistors 94 as described in FIGS. 4 and 5. The digital PCB 60 includes control circuitry 102. In certain embodiments, the control circuitry 102 may include a field-programmable gate array. The control circuitry 102 includes processing circuitry that execute instructions stored in a memory (e.g., on a non-transitory computer readable medium). The control circuitry 102 is utilized in the acquisition of the image data from the detector sensor assembly 20, receiving feedback from the temperature regulation device 51, and controlling or regulating the temperature regulation device 51. As depicted, the control circuitry 102 includes multiple proportional integral derivative (PID) controllers 104 (e.g., PID controller 106 (PID1), PID controller 108 (PID2), PID controller 110 (PID3)). The PID controllers 106, 108, 110 form closed PID controls loops with the respective heating elements 82, 84, 86 and respective thermistors 96, 98, 100. The PID controllers 104 receive a temperature set point 112 as an input (e.g., from the memory) and provide output control signals to the respective heating elements 76 to heat the heating elements 76 to achieve the temperature set point 112. In certain embodiments, a desired temperature range may be provided as the input to the PID controllers 104 and a deadband may be utilized by the PID controllers 104. The PID controllers 104 receive input (e.g., temperature feedback) from the respective thermistors 94 to enable the PID controllers to regulate the heating of the heating elements 76 and, thus, the temperature across the photodiode array 54. In certain embodiments, the temperature set point 112 may be the same for each PID control loop. In other embodiments, the temperature set point 112 may be different for the PID control loops. For example, PID control loops for the heating elements 76 (e.g., heating elements 82, 86) adjacent an edge of the flex circuit 58 may have a different temperature set point 112 than the PID control loop for a centrally located heating element 76 (e.g., heating element 84). In certain embodiments, the control circuitry 102 may have a single PID controller 104 that forms a single closed PID control loop with the heating elements 76 and the thermistors 94.

Figure 7:
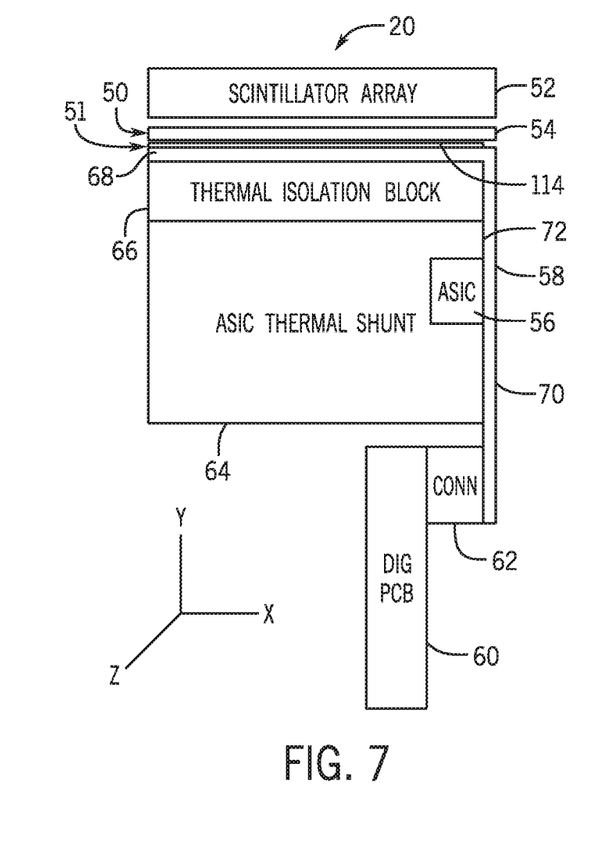
FIG. 7 is a schematic diagram of a side of a detector sensor assembly having a temperature regulation system (e.g., having a positive temperature coefficient (PTC) heater disposed between a photodiode array and a flex circuit), in accordance with an embodiment.
Figure 8:
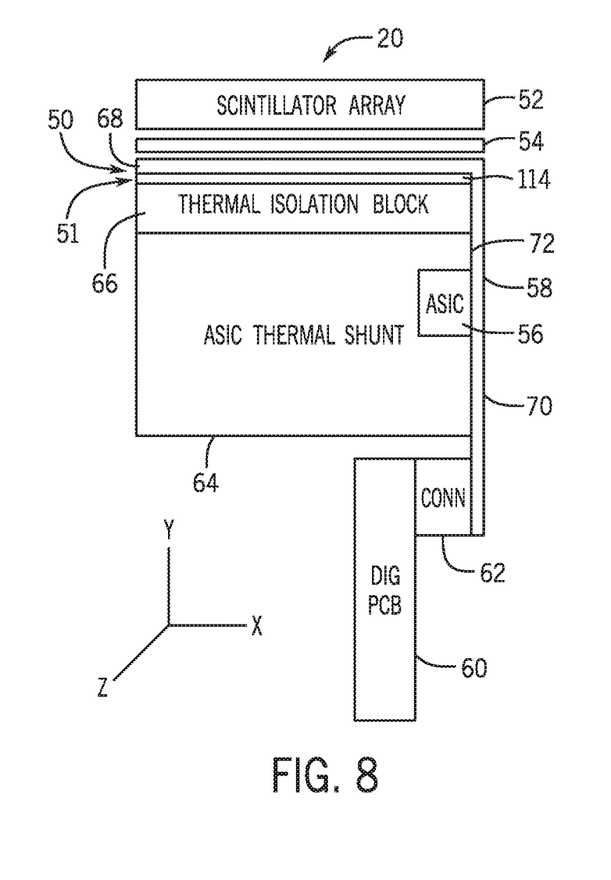
FIG. 8 is a schematic diagram of a side of a detector sensor assembly having a temperature regulation system (e.g., having a PTC heater disposed between a flex circuit and a thermal isolation layer), in accordance with an embodiment.
Figure 9:
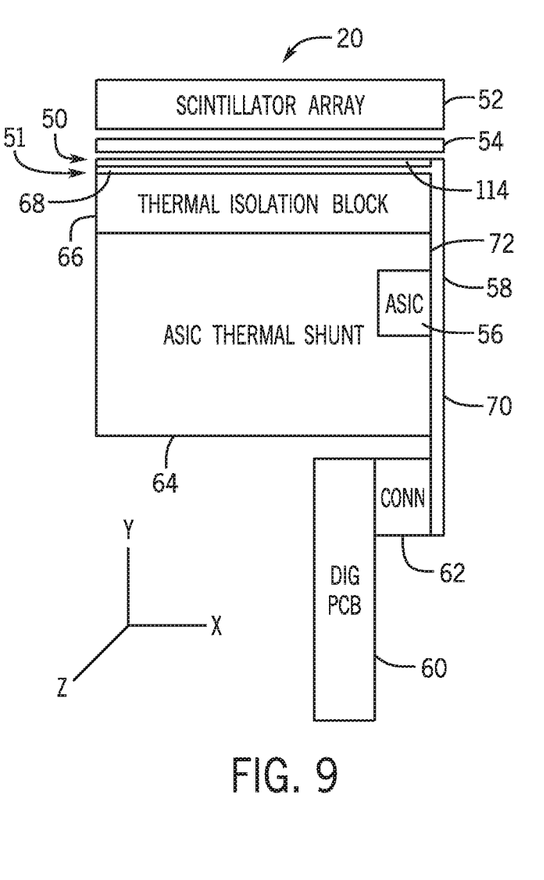
FIG. 9 is a schematic diagram of a side of a detector sensor assembly having a temperature regulation system (e.g., having a PTC heater integrated within the flex circuit), in accordance with an embodiment.
Figure 10:
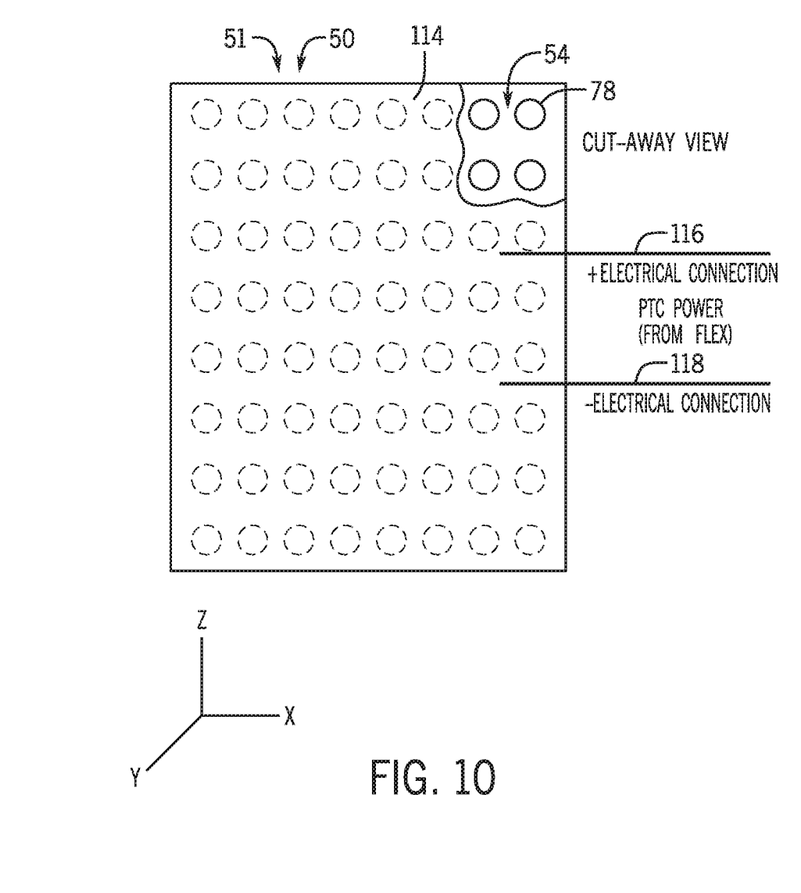
FIG. 10 is a schematic diagram illustrating a photodiode array of the detector sensor assembly of FIG. 7 in relation to the PTC heater, in accordance with an embodiment.

As an alternative to heating elements and thermistors, the detector sensor assembly 20 may utilize as the temperature regulation device 51 a semiconductor device configured to acts as a positive temperature coefficient (PTC) heater to maintain a constant temperature across the photodiode array 54. FIGS. 7-9 are different schematic diagrams of a side of the detector sensor assembly 20 having a PTC heater 114 as the temperature regulation device 51. The PTC heater 114 is configured to self-regulate its temperature to a certain set point. Specifically, the PTC heater 114 increases its electrical resistance at temperatures above a certain level and is able to maintain a constant heating element temperature during load and supply voltage changes. Thus, the PTC heater 114 does not to be externally controlled. As depicted in FIG. 7, the PTC heater 114 is a thin, flexible layer disposed between the photodiode array 54 and the portion 68 of the flex circuit 58. The PTC heater 114 may include holes for forming diode connections. As depicted in FIG. 8, the PTC heater 114 is a thin, flexible layer disposed between the portion 68 of the flex circuit 58 and the thermal isolation layer 66. As depicted in FIG. 9, the PTC heater 114 is integrated within the portion 68 of the flex circuit 58. As depicted in FIG. 10, the PTC heater 114 is power by two conductors 116, 118 in the flex circuit 58.

Technical effects of the disclosed embodiments include providing a temperature regulation system that provides temperature regulation for individual detector elements or sensors (e.g., via localized control and feedback). In certain embodiments, the temperature regulation system includes individual temperature regulation devices associated with each individual detector element that maintain a consistent temperature across a photodiode array of the detector element. The temperature regulation system may enable a faster thermal response for the entire detector, which corresponds to a faster time for the overall CT system to be ready for acquisition. In addition, the temperature regulation system provides a lower cost thermal solution than typical cooling systems.

This written description uses examples to disclose the present subject matter, including the best mode, and also to enable any person skilled in the art to practice the present approaches, including making and using any devices or systems and performing any incorporated methods. The patentable scope is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A detector assembly positionable to receive X-rays from an X-ray source within an imaging system, the detector assembly comprising:
    a plurality of detector elements; and
    a temperature regulation system comprising a plurality of temperature regulation devices, wherein each temperature regulation device of the plurality of temperature regulation devices is associated with a respective detector element of the plurality of detector elements, and each temperature regulation device is configured to independently maintain a consistent temperature across a portion of a respective detector element;
    wherein each detector element of the plurality of detector elements comprises a scintillator array configured to convert X-rays into lower energy light photons, a photodiode array configured to convert the light photons into analog electrical signals, electronics configured to receive the analog electrical signals and to convert the analog electrical signals to digital signals, and a flex circuit coupled to both the photodiode array and the electronics and configured to provide the analog electrical signals to the electronics;
    wherein each detector element comprises a thermal shunt coupled to the electronics and configured to receive heat generated by the electronics, each detector element comprises a thermal isolation layer disposed between the photodiode array and the thermal shunt and configured to thermally isolate the electronics and the thermal shunt from the photodiode array, and a portion of the flex circuit is disposed between the photodiode array and the thermal isolation layer, and wherein a portion of the thermal shunt is disposed between the electronics and the photodiode array.

2. The detector assembly of claim 1, wherein each temperature regulation device of the plurality of temperature regulation devices is configured to maintain a consistent temperature across the photodiode array.

3. The detector assembly of claim 2, wherein each temperature regulation device comprises a plurality of heating elements disposed within the portion of the flex circuit, each temperature regulation device comprises a plurality of thermistors disposed within the flex circuit with a respective thermistor of the plurality of thermistors coupled to a respective heating element of the plurality of heating elements, and each respective thermistor is configured to provide temperature feedback for the respective heating element.

4. The detector assembly of claim 3, wherein the plurality of heating elements comprises a plurality of resistor arrays.

5. The detector assembly of claim 3, wherein each detector element comprises control circuitry coupled to the plurality of heating elements and the plurality of thermistors, wherein the control circuitry is configured to control the plurality of heating elements to a specific set temperature point and to receive the temperature feedback from the plurality of thermistors.

6. The detector assembly of claim 5, wherein the control circuitry is configured to utilize one or more proportional integral derivative control loops to control the plurality of heating elements.

7. The detector assembly of claim 5, wherein the plurality of heating elements comprises a first heating element and a second heating element, the first heating element is located adjacent an edge of the portion of the flex circuit and the second heating element is centrally located within the portion of the flex circuit, and the control circuitry is configured to control the first heating element to a first temperature and to control the second heating element to a second temperature different from the first temperature.

8. The detector assembly of claim 2, wherein each temperature regulation device comprises a semiconductor device configured to act as a positive temperature coefficient (PTC) heater configured to self-regulate a temperature of the PTC heater.

9. The detector assembly of claim 8, wherein the PTC heater is disposed between the photodiode array and the flex circuit or between the photodiode array and the thermal isolation layer.

10. The detector assembly of claim 8, wherein the PTC heater is integrated within the portion of the flex circuit.

11. The detector assembly of claim 1, comprising a heat spreading layer disposed between the portion of the flex circuit and the thermal isolation layer.

12. The detector assembly of claim 1, wherein the detector assembly comprises a computed tomography (CT) detector assembly for a CT imaging system.

13. A computed tomography (CT) detector assembly, comprising:
a detector element comprising:
a scintillator array configured to convert X-rays into lower energy light photons;
a photodiode array configured to convert the light photons into analog electrical signals;
electronics configured to receive the analog electrical signals and to convert the analog electrical signals to digital signals; and
a flex circuit coupled to both the photodiode array and the electronics and configured to provide the analog electrical signals to the electronics;
a thermal shunt coupled to the electronics and configured to receive heat generated by the electronics, wherein a portion of the thermal shunt is disposed between the electronics and the photodiode array;
a thermal isolation layer disposed between the photodiode array and the thermal shunt and configured to thermally isolate the electronics and the thermal shunt from the photodiode array, wherein a portion of the flex circuit is disposed between the photodiode array and the thermal isolation layer; and
a temperature regulation device coupled to the detector element and configured to maintain a consistent temperature across the photodiode array.

14. The CT detector assembly of claim 13, wherein the temperature regulation device comprises a plurality of heating elements disposed within the portion of the flex circuit, a plurality of thermistors disposed within the flex circuit with a respective thermistor of the plurality of thermistors coupled to a respective heating element of the plurality of heating elements, and each respective thermistor is configured to provide temperature feedback for the respective heating element.

15. The CT detector assembly of claim 13, wherein the temperature regulation device comprises a semiconductor device configured to act as a positive temperature coefficient (PTC) heater configured to self-regulate a temperature of the PTC heater.

16. A computed tomography (CT) system, comprising:
a gantry having an opening for receiving an object to be scanned;
an X-ray source attached to the gantry and configured to emit X-rays through the opening; and
a detector assembly attached to the gantry and configured to receive the X-rays, wherein the detector assembly comprises:
a detector element comprising:
a scintillator array configured to convert X-rays into lower energy light photons;
a photodiode array configured to convert the light photons into analog electrical signals;
electronics configured to receive the analog electrical signals and to convert the analog electrical signals to digital signals; and
a flex circuit coupled to both the photodiode array and the electronics and configured to provide the analog electrical signals to the electronics;
a thermal shunt coupled to the electronics and configured to receive heat generated by the electronics, wherein a portion of the thermal shunt is disposed between the electronics and the photodiode array;
a thermal isolation layer disposed between the photodiode array and the thermal shunt and configured to thermally isolate the electronics and the thermal shunt from the photodiode array, wherein a portion of the flex circuit is disposed between the photodiode array and the thermal isolation layer; and
a temperature regulation device coupled to the detector element and configured to maintain a consistent temperature across the photodiode array.

17. The CT imaging system of claim 16, wherein the temperature regulation device comprises a plurality of heating elements disposed within the portion of the flex circuit, a plurality of thermistors disposed within the flex circuit with a respective thermistor of the plurality of thermistors coupled to a respective heating element of the plurality of heating elements, and each respective thermistor is configured to provide temperature feedback for the respective heating element.

18. The CT detector assembly of claim 16, wherein the temperature regulation device comprises a semiconductor device configured to act as a positive temperature coefficient (PTC) heater configured to self-regulate a temperature of the PTC heater.

* * * * *